United States Patent [19]

Brooker et al.

[11] 4,128,628

[45] Dec. 5, 1978

[54] AUTOMATED IMMUNOASSAY

[75] Inventors: Gary L. Brooker; Wesley L. Terasaki; Michael G. Price, all of Charlottesville, Va.

[73] Assignee: University of Virginia Alumni Patents Foundation, Charlottesville, Va.

[21] Appl. No.: 765,348

[22] Filed: Feb. 3, 1977

Related U.S. Application Data

[63] Continuation-in-part of Ser. No. 666,302, Mar. 12, 1976, Pat. No. 4,022,577, and a continuation-in-part of Ser. No. 730,630, Oct. 7, 1976.

[51] Int. Cl.$^2$ ............... A61B 10/00; G01N 33/00
[52] U.S. Cl. ............... 424/1; 23/230 B; 422/71; 195/103.5 R; 424/12; 424/1.5
[58] Field of Search ............... 424/1, 1.5, 12; 23/230 B, 253 R; 195/103.5 R

[56] References Cited

U.S. PATENT DOCUMENTS

| | | | |
|---|---|---|---|
| 3,896,217 | 7/1975 | Johnson | 424/1 |
| 3,940,475 | 2/1976 | Gross | 424/1 |
| 3,950,134 | 4/1976 | Miles | 23/230 B |
| 3,950,643 | 4/1976 | Charlton | 424/1 |
| 3,989,383 | 11/1976 | Paulson | 23/230 B X |
| 4,009,005 | 2/1977 | Johnson | 23/253 R |
| 4,022,577 | 5/1977 | Brooker | 23/230 B |

Primary Examiner—Benjamin R. Padgett
Assistant Examiner—Christine M. Nucker
Attorney, Agent, or Firm—Oblon, Fisher, Spivak, McClelland & Maier

[57] ABSTRACT

An automated immunoassay apparatus which provides: time controlled incubation of a multiplicity of sample solutions, each of which comprise a mixture of (a) a sample, possibly containing an antigen or antibody intended to be assayed; (b) a solution of a known concentration of a tagged antigen or tagged antibody; and when assaying for antigen, optionally; (c) a solution of a known titer of an antibody reactable with said antigen; isolation of incubated samples from additional sample solutions introduced into said apparatus for assay, whereby the system is isolated at a first predetermined signal from a timing device, and whereby the system is reconnected at a second predetermined signal from the timing device, wherein the second predetermined time period is set so as to enable sufficient time to complete a measurement of the amount of tagged material before the next incubated sample arrives in the detector for the next sequential measurement.

16 Claims, 11 Drawing Figures

AUTOMATED IMMUNOASSAY

The invention described herein was made in the course of or under a grant from the Department of Health, Education and Welfare.

CROSS-REFERENCE TO RELATED APPLICATION

This application is a Continuation-in-Part of application Ser. No. 666,302 filed Mar. 12, 1976 (now U.S. Pat. No. 4,022,577), and Continuation-in-Part of application Ser. No. 730,630 filed Oct. 7, 1976.

BACKGROUND OF THE INVENTION

1. Field of the Invention

The present invention relates to a method for assaying the concentration of antigen or antibody in a sample by an immunoassay technique. More particularly, the present invention relates to automated immunoassay techniques for measuring antigen or antibody concentration via selective antibody-antigen reactions, under conditions which permit extremely rapid analysis.

2. Description of the Prior Art

In U.S. application Ser. No. 666,302, filed Mar. 12, 1976 (now allowed), applicants disclosed and claimed a technique and apparatus for radioimmunoassay of antigens wherein the antigen containing solution was admixed with a solution of a known concentration of an antigen tagged with a radioactive isotope and a solution of a known titer of an antibody reactable with said antigen. Further consideration of the apparatus and technique has now led to the understanding of its applicability for the assay of antibodies as well. Moreover, it is now understood that by modifying the originally disclosed apparatus and process, good results can be attained either by radioactive tagging of the antigen or antibody, or by tagging the antigen or antibody with one of a multiplicity of suitable tagging agents, such as ultraviolet, visible or infrared absorbing compounds, radio-opaque dyes, enzymes, proteins, fluorescent, luminescent or radioluminescent compounds, other antibodies or other antigens, etc. Moreover, it is now understood that the technique of making the first measurement which activates the timing mechanisms and which, thereby, activates the control mechanism for the process, need not be a radioactivity sensor but can be any of a multitude of suitable detection techniques.

It is the purpose of the present disclosure to discuss these important improvements to the original system.

SUMMARY OF THE INVENTION

Accordingly, one object of the present invention is to provide a fully automated and continuous assay method for the rapid and accurate determination of antigen or antibody through specific antibody-antigen interactions, using a novel immunoassay technique.

Another object of the present invention is to provide apparatus which is designed for the rapid, automatic immunoassay of antigen or antibody by specific antigen-antibody reactions.

Briefly, these objects and other objects of the invention as hereinafter will become more readily apparent can be attained by a process which comprises incubating for a predetermined time period, a multiplicity of sample solutions, each of which comprises a mixture of (a) a sample possibly containing an antigen intended to be assayed; (b) a solution of a known concentration of a tagged antigen; and when assaying for antigen, optionally, (c) a solution containing a known titer of antibody reactable with said antigen, the concentration of said antibody being selected so as to form an incubated sample containing an antibody-antigen complex, and possibly containing unreacted antigen and tagged antigen, if said sample contains an antigen;

directing said incubated sample into an activating detector which is capable of determining the presence of said sample and which is capable of activating a timing means upon detection of said sample in said detector;

isolating said incubated sample from any additional samples being incubated on a predetermined signal from said timing means;

separating said incubated solution into a first portion containing antigen or antibody which has not been complexed during the said incubation and a second portion containing antigen or antibody which has been complexed during said incubation;

directing one of said portions into a measuring detector, detecting the amount of tagged material in said portion while said portion is maintained in a virtually static condition, and recording said measurement;

evacuating said portion to waste;

directing a subsequent incubated sample into said activating detector on a second predetermined signal from said timing means so that the next subsequent incubated sample to be assayed arrives in the activating detector for the next measurement after the previous measurement in completed; and comparing the measurement with precalibrated values to determine the quantity of antigen being assayed.

This process can be effectively carried out by the use of apparatus which comprises means for time controlled incubation of a multiplicity of sample solutions, each of which comprise a mixture of (a) a sample, possibly containing an antigen or antibody intended to be assayed; (b) a solution of a known concentration of a tagged antigen or tagged antibody; and when assaying for antigen, optionally; (c) a solution of a known titer of an antibody reactable with said antigen;

activating detector means for determining the presence of the incubated sample and for activating a timing means upon detection of said sample at a detection station;

means for introducing said incubated sample into said activating detector means;

timing means, which is activatable by said activating detector means when said detector means detects the presence of the incubated sample at a detection station, for generating control signals at predetermined time sequences;

means for separating said measured solution into a first portion containing antigen or antibody which has not been complexed during the said incubation, and a second portion containing antigen or antibody which has been complexed during said incubation;

means for introducing one of said portions from said separating means into a measuring detector means;

measuring detector means for detecting the amount of tagged material in said portion while said portion is maintained in a virtually static condition;

recording means coupled to said detector means for recording the amounts of tagged material in said measuring detector means;

means for isolating said incubated sample from additional sample solutions introduced into said apparatus for assay, wherein said isolating means is activatable by a control signal emitted from said timing means, whereby said isolating means isolates the system at a first predetermined signal from said timing means, and whereby said isolating means reconnects the system to said incubation means at a second predetermined signal from said timing means, wherein the second predetermined time period is set so as to enable sufficient time to complete said measurement before the next incubated sample arrives in the said detector means for the next sequential measurement; and means for flushing said sample from said system after said measurement thereof so as to prepare said detector for the next sequential sample for said measurement.

DETAILED DESCRIPTION OF THE PREFERRED EMBODIMENTS

In the following description, the reference numerals refer to the numerals in the several Figures.

According to this invention, immunoassay is carried out continuously and automatically, including reagent addition, separation of bound ligand from the total incubation mixture, and final measurement determinations on line without any human intervention. The first results become available within 3-30 minutes, and in some instances, faster, and a new sample is thereafter processed every one and one-half to three minutes. One system according to the present invention can process over 400 samples per day, a rate which would be difficult to achieve by several technicians using presently available conventional equipment.

In accordance with the present embodiment of this invention, immunoassay of a multiplicity of samples is achieved. The sample which is suspected to contain an antigen, or an antibody to be assayed, is first mixed with a solution of a detectable antigen or antibody. The antigen or antibody can be made detectable by reacting a detectable ligand therewith, such as a radioactive isotope, a fluorescent compound, a luminescent compound, a bioluminescent compound, an enzyme, another antibody, or another antibody, or by a variety of known techniques.

The mixture is incubated so that the detectable antigen or antibody is complexed with the antibody or antigen, if any, in the sample being assayed. It is possible, for instance, to use a detectable antigen to complex with possible antibodies in the sample. Alternatively, it is possible to use a detectable antibody to complex with possible antigens in the sample. Still alternatively, it is possible to mix and incubate an antibody solution and a solution of detectable antigen with the sample being assayed, which is suspected of containing antigen, so that the detectable antigen competes with any sample antigen for the available antibody.

The measurement is effected by reliance on the tagging. In the parent application Ser. No. 666,302, the "tagged" materials consisted only of radioactive isotopes. To the extent that the sample being assayed contained antigens, the antigen would complete proportionately with the radioactively tagged antigen for the available antibody. Separation of the incubated sample into two portions, one containing antigen-antibody complexes and the other containing unreacted antigen, and measurement of the quantity of radioactivity present in one of the portions gave a proportional measurement of the quantity of antigen present in the sample being assayed.

Although tagging with a radioactive isotope is an effective means of making the measurement, it is now understood that there are many other tagging means that might also be used. For instance, suitable tagging techniques which can be used include tagging with ultra violet, visible or infrared absorbing compounds, enzymes, enzyme substrates, fluorescent compounds, luminescent or bioluminescent compounds, proteins, other antibodies or other antigens. If the sample being assayed is suspected of containing an antigen, then the tagged antigen solution which is used in conjunction with the solution containing a known titer of antibody, may be tagged with a dye, for instance. In this case, after separation of the complexed antibody-antigens from the unreacted antibody and antigen, a proportional measurement can be made using a colorimeter or a photometer to determine the ratio of color intensity in one of the samples compared with the maximum or minimum color intensity, as the case may be, if the sample being assayed contained no antigen.

If the antigen is tagged with an enzyme, then the measurement can be made by permitting the enzymatic activity of one of the portions to act on a substrate to which the particular enzyme is specific. The resulting product is then measured.

Tagging with fluorescent compounds enables measurement of the proportioning of the complexed from the non-complexed portions by use of a fluorometer. Tagging with other antibodies enables measurement by means capable of detecting said antibodies. Tagging with other antigens enables measurement by means capable of detecting said antigens.

Thus, whereas in the parent application, tagging was recognized as being limited to use of radioactive isotopes, and that such type of tagging provided quite superior results, it is now understood that a wide variety of different tagging techniques could also be suitably used.

The selection of the tagging material is made on the basis of its ability to react with the particular antigen or antibody being tagged, and on the availability of instrumentation which can distinguish between varying concentrations of the tagged material. Moreover, of course, the tagging material selected must not adversely interfere with the antibody-antigen rection.

Suitable tagging materials which can be used include enzymes, such as catalase, glucose oxidase, alkaline phosphatase, hexokinase; fluorescent compounds, such as fluoresceine, umbelliferone, quinine, NADTH, Naphthalene; proteins, such as histone, gelatin, casein; and antigens, such as ATP or dinitrophenol. Also useable are radioluminescent compounds, such as 2-5-diphenyloxazole; radioopaque dyes such as iodopaque, and the like.

Following the incubation of the sample with at least a solution containing the tagged antigen or tagged antibody, it is necessary to separate out the antigen-antibody complex formed, or to separate out the unreacted antibody, or the unreacted antigen. Alternatively, if the incubation is of a mixture of sample, detectable antigen solution, and a known quantity of antibody, then the separation might be of the combination of unreacted antibody and antigen-antibody complex. If the incubation is of a mixture of detectable antigen solution and a sample possibly containing an antibody, the incubated mixture will contain the antigen-antibody complex and unreacted antibody and unreacted antigen. One might separate out the antibody, and the antigen-antibody complex, or one might separate out the antigen and the antigen-antibody complex.

The separation of the desired component is conventionally carried out by adding an adsorbent to the components, or by precipitation or filtration techniques. The adsorbent might be specific for the antigen, or it might be specific for the antibody. A very wide range of adsorbent materials may be used for this purpose, as is well known in the art.

Following separation of one of the components of the incubated mixture, the remainder is measured for the presence of detectable antigen or detectable antibody. The quantity in the measurement is then a measure of the relative quantity of antigen or antibody contained in the sample.

In the parent application Ser. No. 666,302, it was considered necessary to use a solution of known concentration of antibody in combination with a solution of the tagged antigen and the sample solution. It is now understood that while very high sensitivity is attainable with such systems, the use of a solution of known concentration of tagged antigen can be dispensed with for specific systems. Specifically, if the sample is being assayed for specific antigens, it is sometimes superior to use a tagged antibody alone. The antigen solution could be dispensed with if tagged antibody is available and by use of a means for separating antibody from antigen-complexed antibody (e.g., a column containing immobilized antigen).

In the parent application Ser. No. 666,302, it was disclosed that radioactive isotope tagging can be used for the dual purposes of measuring the proportions of complexed and unreacted antibodies and antigens, and for process control of the system. Thus, the total incubated mixture, including total amount of tagged antigens, the solution of the antibody and the sample being assayed, were moved into a radioactivity detector means. The appearance of the incubated mixture in the crystal detector activated a timing mechanism which in turn activated certain valves which isolated the measuring and incubation sections of the system. The timing mechanism also controlled other processing conditions.

The same radioactive isotope tagged material was also used to measure the proportioning of the complexed antibody-antigens, from the unreacted materials. Thus, after the incubated mixture was passed through a radioactivity detector to set the system controls, it was then passed into a separation means to separate the complexed from the uncomplexed antibody-antigen combinations. One of the portions was then transferred to the radioactivity detector means in order to determine the degree of proportioning. In contrast, it is now understood that for specific systems, different criteria can be relied upon to measure the presence of the sample for purposes of activating the timing mechanism, and for measuring the degree of proportionation.

A detecting station is located subsequent to the incubation apparatus. When the sample arrives at the detection station, its presence must be sensed and control signals activated. Instead of relying on radioactive isotope detection to determine the presence of a sample at the detection station, it is possible to rely on any of a number of alternate criteria for making a similar determination and system activation. For instance, since each incubated sample is separated by a space containing a buffer solution, it is possible to measure the difference in conductivity between the buffer and the incubated mixture. Thus the arrival of the incubated mixture at the detection system is announced by an abrupt change in electrical conductivity or by an abrupt change in pH, since the pH of the incubated sample will be different from the buffer solution spacers between samples. Alternatively, the differing polarization of the samples and buffer can be utilized. Other suitable techniques include the concept of admixing a measurable cation into the sample or into the buffer, or by the addition of various absorbing compounds, fluorescent materials, luminescent materials, into the sample or buffer, or by reliance on the differing refractive indices, differing diffraction patterns, which differences can be enhanced by the addition to either the buffer or the sample of inert particles, emulsifiers, or even small air bubbles. Alternatively, the same tagged material which is used to measure the proportioning of the incubated sample between complexed and non-complexed antibodies and antigens, can be used to measure the presence of the incubated sample at the detection station. Thus, the activating detector means may be a conductivity detector, pH meter, a photodetector, a refractometer, fluoroscope, a luminescent detector, or the like.

Thus, the sample is mixed, incubated and passed into a detection station. The presence of the incubated sample is detected by change in electrical conductivity, photometrically, diffraction, etc. or by the presence of the tagged material. The detector activates the timing means which controls the system valves. The incubated mixture is then passed to a separator where the complexed and non-complexed materials are separated into two portions, and one portion is passed into a measuring detection means wherein the quantity of tagged material is detected.

A wide variety of antigens and antibodies and complexes of the same can be treated by the methods of this invention. For instance, suitable antigens and their corresponding antibodies and complexes which can be separated include:

| Pituitary hormones | Calcitropic hormones |
|---|---|
| Growth hormone | Parathyroid hormone (PTH) |
| Adrenocorticotropic hormone (ACTH) | Calcitonin (CT) |
| Melanocyte-stimulating hormone (MSH) | Gastrointestinal hormones |
| α-MSH | Gastrin |
| β-MSH | Secretin |
| Glycoproteins | Cholecystokinin-pancreozymin (CCK-PZ) |
| Thyroid-stimulating hormone (TSH) | |
| Follicle-stimulating hormone (FSH) | Enteroglucagon |
| Luteinizing hormone (LH) | Vasoactive tissue |

-continued

| | |
|---|---|
| Prolactin | hormones |
| Lipotropin (LPH) | Angiotensins |
| Vasopressin | Bradykinins |
| | Hypothalamic-releasing factors |
| Oxytocin | Thyrotropin-releasing factor (TRF) |
| Chorionic hormones | |
| Human chorionic gonadotropin (HCG) | Steroids |
| Human chorionic somatomammotropin (HCS) | Aldosterone |
| Pancreatic hormones | Testosterone |
| Insulin | Dihydrotestosterone |
| Proinsulin | Estradiol |
| C-peptide | Estrone |
| Glucagon | Estriol |
| | 2-Hydroxyestrone |
| Prostaglandins | Enzymes |
| Thyroidal hormones | C₁esterase |
| triiodothyronine | Fructose 1,6-diphosphatase |
| Thyroxine | Virus |
| Drugs | Australia antigen (HAA) |
| Digoxin | Tumor antigens |
| Digitoxin | Carcinoembryonic antigen |
| Morphine | α-Fetoprotein |
| LSD | Serum proteins |
| Cyclic nucleotides | Thyroxine-binding globulin |
| cAMP | Immunoglobulin G (IgG) |
| cGMP | Albumin |
| cIMP | Other |
| cUMP | Intrinsic factor |
| | Rheumatoid factor |
| | Folic acid |
| | Neurophysin |

Instead of a single antibody or a single antigen, a plurality of different antigens or antibodies can be simultaneously assayed by using two or a plurality of different tagged antigens or tagged antibodies.

The sample intended to be assayed may have been obtained from such biological sources as blood, sera, urine, plasma, ascities or the like which is suspected of containing specific antigens or antibodies.

The antibody or antigen solution of known concentration which is tagged by the tagging material can be obtained from known, commercial sources, or can be prepared by techniques which are known in the art. The concentration of the antibody is selected so as to be insufficient to react with the total quantity of the antigen in the sample being assayed. Alternatively, if the antibody is being assayed, then the tagged antigen solution is provided in excess of the expected antibody concentration. In the case of tagged antibody it is provided in excess of the antigen concentration being measured (See Miles, L.E.M. & Hales, C.N. 1968 Nature 219, 186-9).

Figure 1:
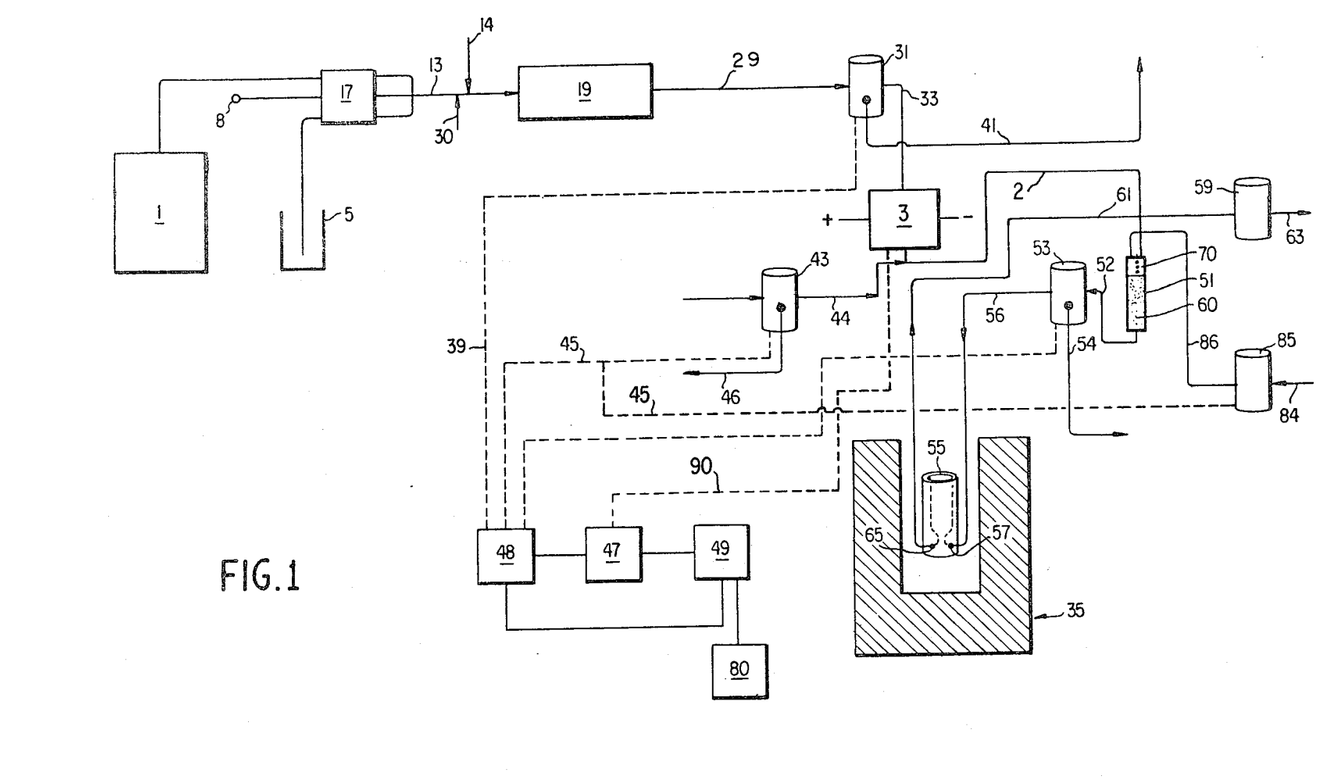
FIG. 1 is a schematic diagram of one type of apparatus according to this invention.

Referring now to the drawing of this application for further understanding of the present invention: The invention will now be described from the point of view of assaying for an antibody using a radioactively tagged antigen. The detection of the sample is measured by conductivity changes and the measurement of the sample after separation of the complexed from non-complexed antigen and antibodies, is made by radioactivity detection. It will be understood, however, that the apparatus and procedure is equally applicable to assaying for an antigen using a tagged antibody, or assaying for an antigen using a tagged antigen and a solution of a known concentration of an antibody.

A tagged antigen containing solution is maintained in container 1. Isotopic tagging of the antigen can be effected by conventional techniques such as by reacting the antigen with moieties that will leave residual amounts of $^{125}I$ or $^{131}I$, or any other suitable radioactive isotope as is known in the art such as $^{75}Se$, $^{3}H$, $^{14}C$, or $^{32}P$. Alternatively, non-radioacitve "tags" may be used provided that there are suitable detection means. Examples are luminescent, bioluminescent, ultraviolet, visible and infrared adsorbing compounds, etc.

The concentration of the tagged antigen solution can vary from one millimole to the limits of concentrations of isotope detectable by the radioactivity detection, usually one femtomole. Instead of a single antibody or a single antigen, two or a plurality of different tagged antigens and different antibodies can be used in combination to give a simultaneous multiple assay. Representative of the tagged antigen systems which might be used include: $^{125}I$-Digoxin, $^{131}I$-Thyroxine, $^{125}I$-secretin, $^{32}P$-cyclic AMP, $^{131}I$-Insulin, $^{125}I$-Glucagon, $^{75}Se$-Cortisol, $^{125}I$-Angiotensin I, $^{125}I$-Carcinoembryonic antigen, $^{125}I$-Somatostatin, $^{131}I$-Insulin, $^{131}I$-Triiodothyronine, $^{125}I$-Thyroxine, $^{125}I$-Growth Hormone, $^{125}I$-cyclic AMP, $^{131}I$-cyclic GMP, $^{125}I$-Morphine, $^{125}I$-Vasopressin, $^{131}I$-Aldosterone derivatives and their respective antibodies. The antigens and antibodies could be contained in sera, urine or buffers commonly used in the presently known art of radioimmunoassay such as sodium acetate, Tris-HCl, Barbital, Phosphate, MES, TES, etc. The samples possibly containing the antibody are picked up by pipette 8. The sample being assayed could be measured at several dilutions such as 1:1, 1:2, 1:5, 1:10, 1:100, 1:1000, etc. A buffer solution is maintained in cup 5. Intermittently, samples of antibodies to be assayed are picked up at point 8 and brought into the system by the peristalic pump 17. The solution of tagged antigen is picked up from 1 and mixing occurs in conduit 13. Each intermedient sample is separated by a space filled with a buffer solution which is taken from 5.

After the solutions are mixed by the pumping action, the mixture is passed through conduit 13 and into an incubation chamber 19 where the mixture will be held under standardized conditions for a fixed predetermined incubation time period.

The incubation chamber 19 may take many forms, however, one of the most advantageous is a long coil-like conduit, not shown, which is held at a predetermined incubation temperature. The flow rate of the sample solution through the incubation coil may be adjusted so that the reaction is sufficiently completed, or at a constant fraction of the maximal reaction, by the time the sample solution traverses the length of the conduit. A multitude of sample solutions can be present in the incubation conduit at the same time, each separated by a buffer solution space. The buffer space not only separates sample solutions, but also picks up tailings so that the next succeeding sample will not be contaminated. Since the solutions in the incubation coil are moving in laminar flow, there is, of course, a potential flow problem with the fluid inthe center of the tube moving at a faster rate than at the edges. This potential problem can be quite easily dissipated by intermittently introducing bubbles in regularly spaced intervals into conduit 13, through bubbler 14, which serves to move the fluid along at a more uniform rate. This technique is disclosed in Skeggs, U.S. Pat. Nos. 3,797,149 and b 2,879,141.

The incubation temperature will, of course, depend upon the particular antibody-antigen system under study. In general, however, the incubation temperature may vary from 0° to 60° C., and often incubation can be effected at room temperature.

The flexibility of this system is quite excellent and the system may be used for continuous assay of different antibody-antigen systems. Thus, each sample solution extracted and introduced into conduit 13 may contain a different antigen-antibody system. It is not even necessarily required to readjust the incubator conditions each time the antibody-antigen system is changed. It is only necessary that the calibration of the equipment for standardized samples be made under the same conditions as those used for the unknown. That is to say, it is not necessary that the incubation period be sufficient for the reaction to go to completion. It is only necessary that the incubation period for the samples be the same as the samples used for calibration. This is in sharp contrast to prior systems which, in general, required the reactions to go to completion for success. The length of incubation may vary from 1 minute to 30 minutes and even up to 1 day, depending upon the particular system. In general, if the incubation time is unacceptably long, it is possible to speed incubation by the addition of more antibody or antigen or altering the temperature.

Alternatively, the sample can be moved into one of a plurality of containers which is held under predetermined incubation conditions, after which a pipette or similar device removes the incubated sample from the container and moves it through conduit 29 toward the isolating valve 31.

At the termination of the incubation period, the sample is passed through conduit 29 into an isolation valve or by-pass valve 31. The driving force for the movement of the sample through the system to this point is usually due to the pressure created by the peristaltic pump.

The isolation or by-pass valve 31 connects the conduit 29 with conduit 33 and, alternatively, with conduit 41 to waste. At the start of the flow system, valve 31 is opened to conduit 33 and the incubated sample is directed into a conductivity detector 3. The conductivity of the fluid passing through the conductivity detection station 3 is continuously monitored. Since each sample is separated by a buffer solution, the conductivity of the sample being assayed is necessarily different from the buffer spacer. By detecting abrupt changes in conductivity, the detector 3 can determine the presence of a new sample. The conductivity detector comprises a chamber containing a pair of platinum electrodes and has an ohmmeter placed across the electrodes. As the solution passes through the chamber, a change in resistance occurs which is detected by the electrodes. Upon detection of the new sample, the detector triggers a predetermined timing sequence which begins scaling the sample for a predetermined period of time, usually 1 minute or less. This timing means 48 is set after a comparator circuit 47 indicates that the threshold conductivity is present. Control signals from the timing means 48 thereafter set off various valves in a sequence necessary to cause the sample solution to be brought through conduit 2 to a separator 51, where a portion of free isotope tagged antigen will be separated from a portion of antigen-antibody and tagged antigen-antibody complexes. The separation technique is more fully described in parent application Ser. No. 730,630 filed Oct. 7, 1976 and the data with respect thereto is incorporated herein by reference. Thereafter, one of the portions will be brought through conduit 52, through fill valve 53 and conduit 56 into a small reservoir cup 55 in a radioactivity detector 35 where the amount of radioactivity is measured for a predetermined time period, about one minute or less.

The amount of radioactivity detected is compared to standard curves which had been previously constructed from known titers of solutions. The present system assumes that flow characteristics are sufficiently constant and stable. The timing for each sample is exactly the same and is not influenced by small variations in the pumping rate, which can occur over long periods of time.

The timing means 48 measures predetermined time sequences, sending out control signals through line 39 to activate the isolation valve 31, which thereby isolates the measurement portion of the system from the incubation portion of the system. The time sequence measured before valve 31 is activated, is sufficient to at least enable the entire sample to pass into the detector 35 before the measurement system is isolated. In other words, the valve 31 will usually close at some point in time as buffer solution spacers which separate adjacent sample solutions to be measured are passing through the valve 31.

A recording means 49 is provided which is coupled to the comparator circuit 47 and the timing means 48, which is used for recording the amount of radioactivity in the static measurements. These measurements will be used to determine the amount of specific antibody in the unknown sample using a computer 80 which is interfaced to the recording means 49 and timing means 48.

After the isolation valve 31 is closed, thereby diverting the feed from conduit 29 into waste conduit 41, a means can be provided for increasing the speed of the sample solution already in conduit 33. In FIG. 1, this means takes the form of a high flow rate buffer solution inlet valve 43 which is opened simultaneously as the isolation valve 31 is closed, by a predetermined signal from timer 48 from line 45. A solution at relatively high speed enters through conduit 44 into the conduit 33. The high flow rate buffer solution pushes the sample solution through conduit 2 into and through a separator column 51. This high flow rate may be needed because the resistance of the separator column might otherwise prevent free flow of the solution therethrough. The high speed turbulent buffer solution also acts to wash any tailings from the sample solution into the separator column 51, so as to prevent contamination of subsequent sample solutions. In general, the high flow line can feed buffer at a rate of 0.5 ml/min to 50 ml/min and preferably 3 ml/min to 10 ml/min.

The flow rate through the separator column 51 is controlled by the absorbent properties of the column and the hydrostatic head created by the outlet of conduit 54 when the air trap valve 85 is open to connect conduit 86 with conduit 84 which is at atmospheric pressure. The air trap valve 85 is energized simultaneously as the high flow buffer inlet valve 43 is actuated and the isolation valve 31 is closed. This causes the hydrostatic pressure to increase in the column 51 and thus the rate of flow through the column 51 increases. The flow rate now clearly equals the flow rate of the high flow buffer line 44.

The separator column 51 serves to separate the sample solution into two portions: a first portion containing unreacted antigen which has been tagged with the isotope, and a second portion containing the antibody-tagged antigen complex. This separation can be accomplished by a variety of means, some conventional and some not conventional, such as that described in the parent applications Ser. No. 666,230 and Ser. No. 730,630.

The residual sample is eluted from separator 51 by the high flow rate buffer and passes through conduit 52 into fill valve 53 which had been opened by a predetermined signal from circuit 90 from timing means 48. Once the entire eluted portion passes through the fill valve 53, it is again closed, thereby diverting additional buffer coming from the separation column 51 to waste through conduit 54. The column is now ready to receive the next sample. The portion being measured is thus passed into the static measurement section 55 of the radioactivity measurement detector 35 through conduit 56. The static measurement section 55 is a cup having an inlet aperture 57 situated at the base thereof. The residual sample flows from valve 53 through line 56 and into the cup 55 through lower aperture 57. After the separated portion of the sample fills the cup, a radioactivity level count for a predetermined time which is controlled by timing means 48 is made and recorded by recorder 49.

At a predetermined time during the time interval, when the radiation level is being determined, timing means 48 sends a control signal to by-pass valve 31 which reconnects conduit 29 with conduit 33 and permits the next sequential sample solution to begin its transit to the detector 35. At a predetermined time after conduit 29 is reconnected with conduit 33, the timing means 48 sends a signal and valve 59 is opened, which connects conduit 61 with conduit 63 which is connected to a vacuum source developed by the peristaltic pump pumping The solution in the cup 55 is thereby rapidly evacuated through exit port 65 and is disposed of. The control mechanism can be set, if desired, such that at the completion of one control sequence, and hence completion of analysis of one sample, the indication level must return to a predetermined minimum base line before the mechanism can be reactivated to begin the analysis of the next sample.

In the above-discussed arrangement, the inside walls of cup 55 may be made of a non-adhering material such as Teflon or polyphenylenesulfide. Moreover, the design of the cup with the inlet and outlet apertures situated at the base of the cup, functions to avoid splashing so that the cup will empty quite cleanly even without the introduction of the buffer wash solution. Simultaneous with the activation of valve 59, the timing means sends a signal to stop the recording means 49 and causes the recording means to transfer the accumulated counts to computer 80 for data processing as determined by the software programs. The recording means 49 then resets and is ready to record data for the next sample.

Before the isolation valve 31 is reopened, the high flow rate buffer inlet port 44 is closed by a control signal from the timer. When the isolation valve 31 is reopened, connecting conduits 29 with 33, the pressure in conduit 33 approximates that in conduit 29 so that there is no sudden backwash through the incubation system. Similarly, when the by-pass valve 31 is in its closed position, thereby connecting conduits 29 with 41, the pressure in conduit 41 approximates that in conduit 33 since the outlets of conduit 41 and conduit 54 are physically held at the same hydrostatic pressure head. Thus, the flow rate of samples is not altered when valve 31 is energized or deenergized. A timing sequence provides for a difference in time between the shut off of the isolation valve 31 and the shut off of the high flow stream valve 43 and energizing of the column air trap valve 85 sufficient to allow conduit 33 to reach the same hydrostatic pressure as conduit 29 so that backflow or alteration in flow rate does not occur when the conduits 29 and 33 are reconnected.

The major advantage of the present method is that it provides a fully automated procedure for the measurement of antibody or antigen concentration in a test sample, in only a fraction of the time previously required by conventional immunoassay techniques. The present method makes it possible to run a series of tests of widely varying antigen-antibody interactions without any disruption in continuous operation of the apparatus. Consequently, the system does not require the control of a skilled operator, and even unskilled labor can be used to perform the relatively simple tasks required to set up the present system. Since there are literally hundreds of drugs, hormones and biochemically important compounds currently measured by manual immunoassay such as analyses of digoxin, insulin, angiotensin I, thyroxine, cyclic AMP, and the like, the present method provides a means for rapidly and accurately conducting these analyses.

This system also allows the simultaneous detection of several antibodies in the same sample. In this instance, several different isotopes are used with the different antigens. The radioactivity detector isotopes are used with the different antigens. The radioactivity detector will thus detect the different levels of radioactivity emitted by each of the isotopes and by computerized selectivity, simultaneous determination of two or more antibodies can be made.

Having generally described the invention, a more complete understanding can be obtained by reference to certain specific examples, which are included for purposes of illustration only, and are not intended to be limiting unless otherwise specified.

Assays for digoxin, cyclic AMP, cyclic GMP, insulin, angiotensin I and thyroxine are easily performed with this process. In these cases, the sample, isotope solution and antisera were drawn for 30 seconds with a 2½ minute wash between samples. The timing means was preset. Air bubbles were introduced at the rate of 0.32 ml/min into conduit 14. The conduit 63 was pumped at 3.9 ml/min to create suction to rapidly evacuate the static counting cell 55 when valve 59 was opened. Table I provides the essential details of these assays with regard to reagents, and flow rates. The coefficient of variation for these assays was about 2%.

Table 1

| | | | | | | | | | |
|---|---|---|---|---|---|---|---|---|---|
| REAGENTS FOR THE IMMUNOASSAY | | | | | | | | | |
| | | | | | | 0.23 ml/min 7.8 ml/min | | | |
| | | | | | | Buffer Solutions | | | |
| Flow Rate→ | 0.1 ml/min Compound (Sample) | 0.1 ml/min $^{125}$I-Radioligand (0.2 Ci/ml 8) | 0.1 ml/min Antisera 5 | Separation Column 60 | Buffer Line 30 | High Flow 44 | Counts Collected for $B_o$ | Time Delay Coil (min) | Temp. |
| | Digoxin | Digoxigenin | 1:30,000 | Ag 1-X8 | Solution 1 | Solution 1 | 3390 | 3 | Ambient |

Table 1-continued
REAGENTS FOR THE IMMUNOASSAY

| Flow Rate→ | 0.1 ml/min Compound (Sample) | 0.1 ml/min $^{125}$I-Radioligand (0.2 Ci/ml 8) | 0.1 ml/min Antisera 5 | Separation Column 60 | 0.23 ml/min Buffer Line 30 | 7.8 ml/min High Flow 44 | Counts Collected for $B_o$ | Time Delay Coil (min) | Temp. |
|---|---|---|---|---|---|---|---|---|---|
| Cyclic AMP | 3-O-Tyrosine ScAMP-TME | 1:2,000 | 100–200 mesh plus charcoal | plus 5mg/ml bovine serum | without Brij-35 | 3325 | 21 | Ambient |
| Cyclic GMP | ScGMP-Tme | 1:1,000 | 60–200 mesh or AG 1-X8 100–200 mesh | albumin | | 2153 | 21 | Ambient |
| Insulin | Monoiodinated Insulin in 100 ml | 2,000 tube commerical antisera | | Solution 2 Brif-35 | Solution 2 without | 1990 | 21 | 39° C |
| Angiotensin I | Monoiodinated Angiotensin I | 1:2,500 | 9 × 45 mm | | | 2290 | 21 | Ambient |
| Thyroxin (T-4) | Monoiodinated Thyroxin | 500 tube commerical antisera in 50 ml | | | | 1540 | 9 | Ambient |

Solution 1 is 50 mM sodium acetate, pH 4.7 containing 0.015% Brij-35. Solution 2 is 50 mM Tris-HCl, pH 9.2 containing 0.015% Brif-35. Thyroxin isotope solution also contained 1:5000 Sodium Merthiolate. Radioligand was dissolved in the Sampler Wash buffer. Antisera were diluted in the Buffer line buffer. ScAMP-TME (2'-O-Succinyl-Cyclic AMP Tyrosine Methyl Ester) and ScGMP-TME (2'-O-Succinyl-Cyclic GMP Tyrosine Methyl Ester) were labeled with [$^{125}$I]. Specific activity was between 100–200 Ci/mmole. [$^{125}$I]-Digoxigenin-3-O-Tyrosine (Sp. act. 1500 Ci/mmole) Monoiodinated Insulin (100 Ci/g), monoiodinated Angiotensin I (687 Ci/g), Thyroxine[$^{125}$I] (118 Ci/g) diluted in either solution 1 or 2.

EXAMPLE 1

Figure 2:
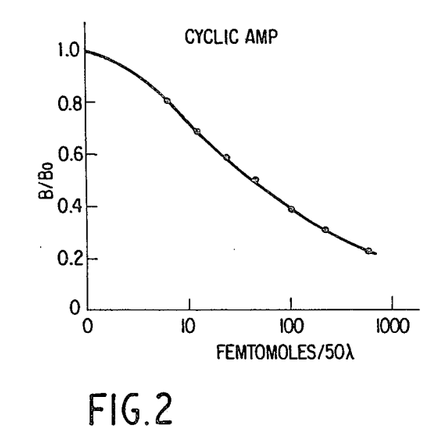
FIG. 2 is a standard curve for cyclic AMP.

FIG. 2 shows a standard curve for cyclic AMP after the standards had been acetylated (500 µl standard + 10 µl triethylamine + 5 µl acetic anhydride). This data and all following data for standard curves is plotted with the concentration of ligand being measured on the abscissa (log) vs the ratio of radioactivity found for standards to that when only the radioligand was present and is presented as the $B/B_o$ ratio. Whether or not the results are normalized by correction using the first count (count 1) the end result is the same, since the first counts would be the same if perfect pumping reproducibility occurred. This compound is thought to be an important mediator of hormone action.

EXAMPLE 2

Figure 3:
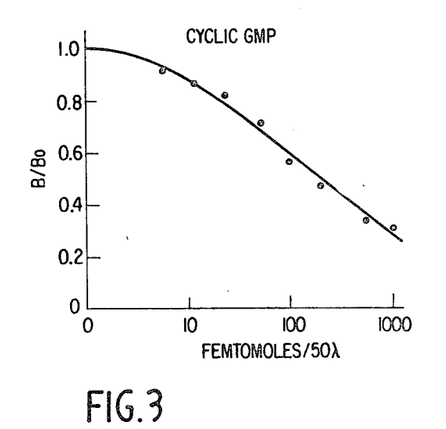
FIG. 3 is a standard curve for cyclic GMP.

FIG. 3 demonstrates a standard curve for cyclic GMP after the standards have been acetylated. It has been suggested that cyclic GMP could be an important regular of processes controlled by the parasympathetic nervous system. In addition, some workers feel that cyclic GMP could be an important indicator of cell growth and its presence in urine could be used to detect certain organs malignancy. The sensitivity shown here is sufficient to measure cyclic GMP in less than 1 microliter of human urine.

EXAMPLE 3

Figure 4:
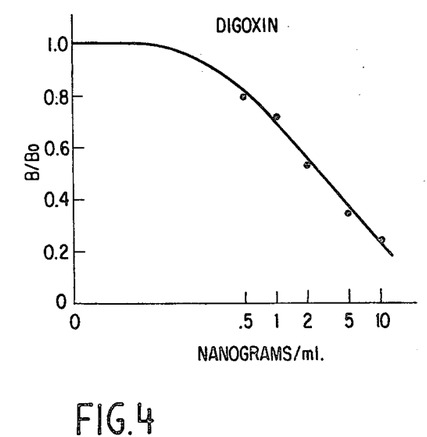
FIG. 4 is a standard curve for Digoxin.
Figure 5:
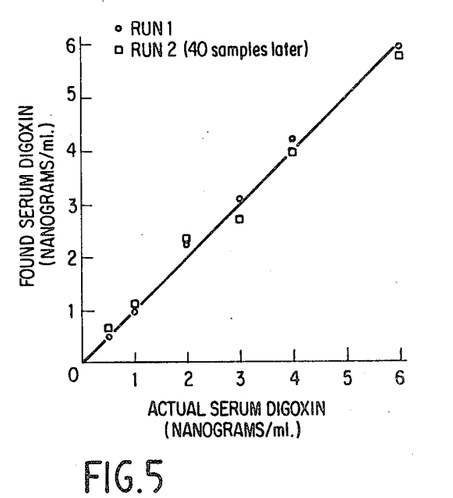
FIG. 5 is a comparison of commercial Digoxin standards with standards determined by the present invention.

FIG. 4 reveals a standard curve for digoxin. It takes less than 4 minutes to do a single determination. Digoxin is an important cardiac glycoside taken by between 3–5 million people in the USA alone. The drug markedly stimulates the heart in people with congestive heart failure. However, the drug is also very toxic to the heart causing rhythm disorders. Serum digoxin levels of 1.4 Ng/ml are considered therapeutic while toxic levels are considered when the serum level rises about 2.5–3 Ng/ml. As can be seen, the assay method has sufficient sensitivity to make this distinction. When commercial serum digoxin standards were repetitively assayed, an excellent correlation was found as shown in FIG. 5. In addition, this FIGURE demonstrates the excellent instrument stability over a long period of time.

EXAMPLE 4

Figure 6:
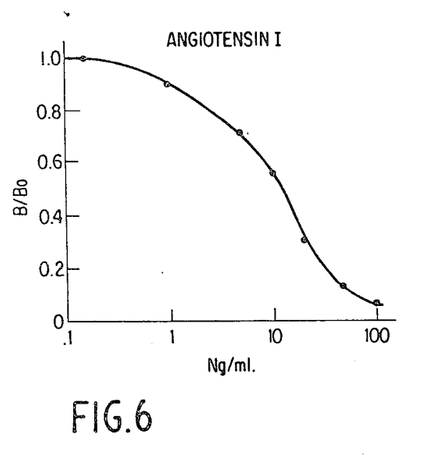
FIG. 6 is an Angiotensin I standard curve.

FIG. 6 illustrates a standard curve for Angiotensin I. While plasma levels are very low, the radioimmunoassay for Angiotensin I is very useful to measure plasma renin activity (PRA). Normal PRA is about 1–6 Ng/ml Angiotensin I/hour and abnormal from 10–100 Ng/ml Angiotensin I/hour. It can be seen that the method can easily make this distinction.

EXAMPLE 5

Figure 7:
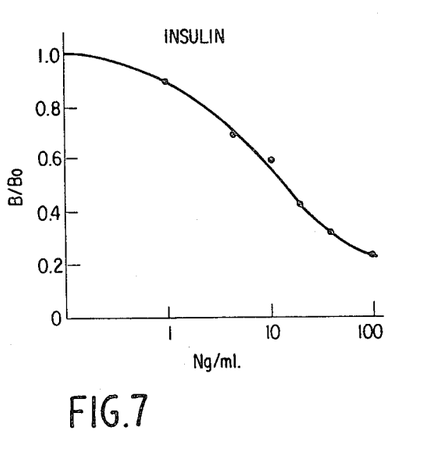
FIG. 7 is an insulin standard curve.

Insulin is an important hormone in glucose homeostasis. Measurement of serum or plasma insulin can be of aid in the diagnosis and management of patients with diabetes. The assay of insulin normally takes several days using conventional techniques. FIG. 7 demonstrates a standard curve for insulin. The total assay time for an individual insulin sample in the present system is only 21 minutes. This could be useful in cases where it is critical to know the serum insulin concentration in order to develop a therapeutic plan for a diabetic patient in insulin imbalance. The sensitivity of this assay is sufficient to monitor insulin in the concentrations normally encountered in clinical medicine.

EXAMPLE 6

Figure 8:
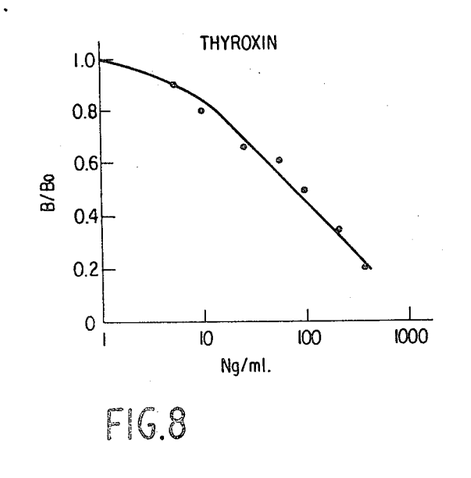
FIG. 8 is a thyroxine standard curve.

FIG. 8 demonstrates a standard curve for thyroxin. The sensitivity of the automated assay is comparable to other radioimmunoassays for thyroxine.

EXAMPLE 7

The automated radioimmunoassay system of the present invention is especially versatile being able to alternately sequentially assay for different substances. The following nine substances at the concentrations indicated were placed in the sampler tray and their respective isotope solutions were drawn as each sample was processed. Incubation was for 21 minutes at 39° C. No delay between samples occurred and it took 27 minutes for all nine samples to be drawn into the instrument.

Notice the excellent reproducibility and the ability to switch between different antigens without any equilibration time needed.

TABLE II

| Sample No. | Compound | Ng/ml | $B/B_o$ |
|---|---|---|---|
| 1 | Angiotensin I | 0 | 1.00 |
| 2 | Angiotensin I | 25 | 0.23 |
| 3 | Insulin | 0 | 1.00 |
| 4 | Thyroxin | 0 | 1.00 |
| 5 | Insulin | 25 | 0.45 |
| 6 | Thyroxin | 0 | 1.05 |
| 7 | Insulin | 25 | 0.42 |
| 8 | Angiotensin I | 25 | 0.20 |
| 9 | Insulin | 0 | 0.95 |

EXAMPLE 8

Figure 9:
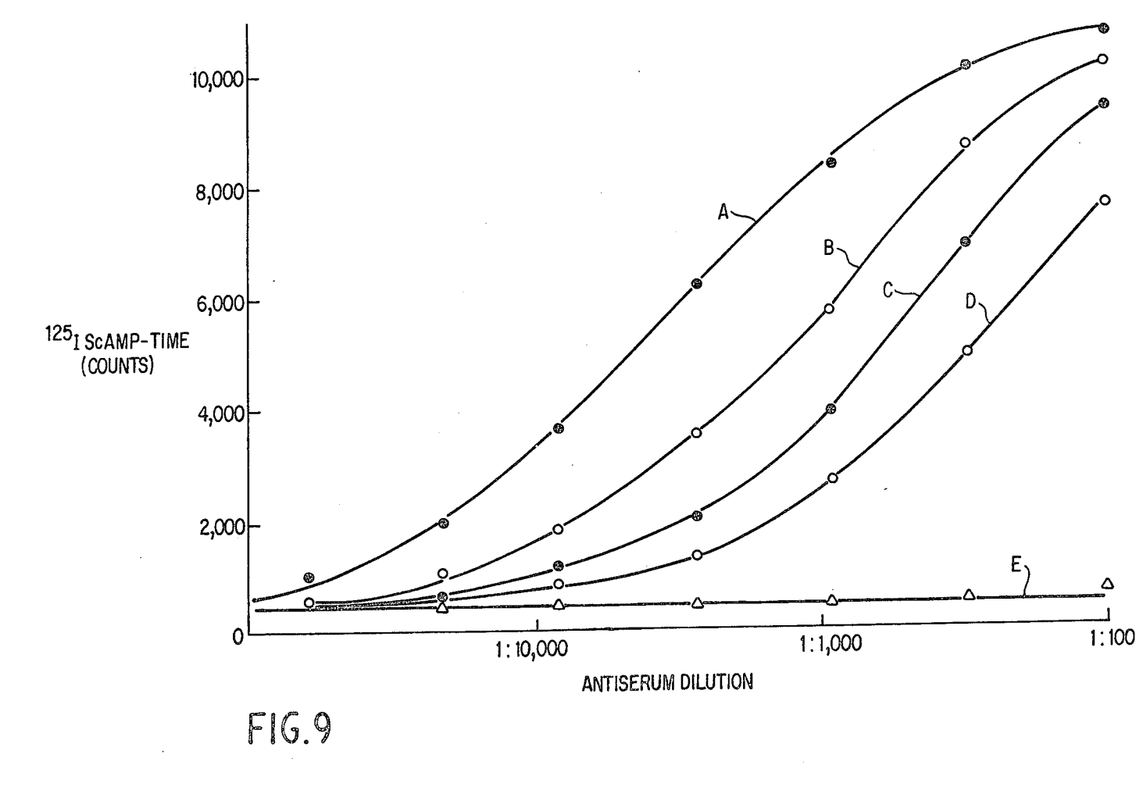
FIG. 9 is a measurement of anti-cyclic AMP antibodies.

FIG. 9 demonstrates the measurement of anti-cyclic AMP antibodies in goat sera harvested from goats immunized with cyclic AMP chemically coupled to human serum albumin. The present automated immunoassay system was used to assay for anti-cyclic AMP antibodies using $^{125}$I-labelled succinyl cyclic AMP tyrosine methyl ester. Curve A is the dilution curve of antiserum bled from a goat 17 days after a booster immunization. B is the curve of antiserum bled 37 days after the same boost. Similarly, curves C and D represent anti-cyclic AMP antibody binding in antisera obtained from a second goat bled 17(C) and 37(D) days after boosting. E represents control serum obtained from an un-immunized goat.

EXAMPLE 9

Figure 10:
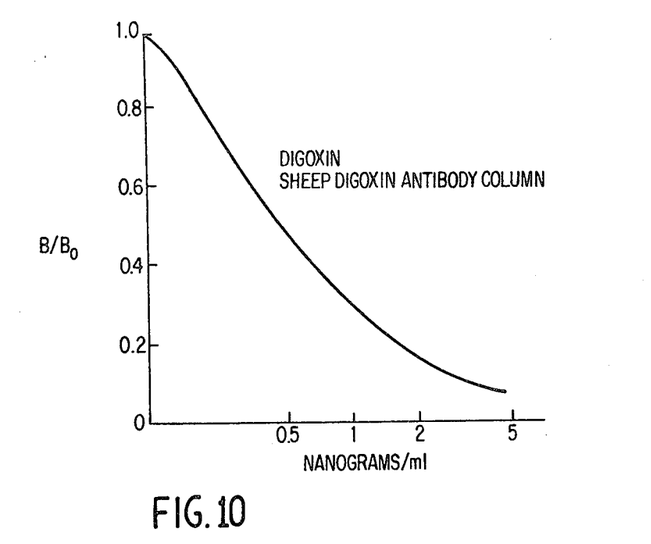
FIG. 10 is a standard curve for Digoxin using anti-digoxin separating column.

FIG. 10 demonstrates an immunoassay technique for digoxin wherein the standard curve is obtained using a separation means wherein antisera to digoxin (raised in sheep) is covalently linked to 50-100 mesh agarose beads.

EXAMPLE 10

Figure 11:
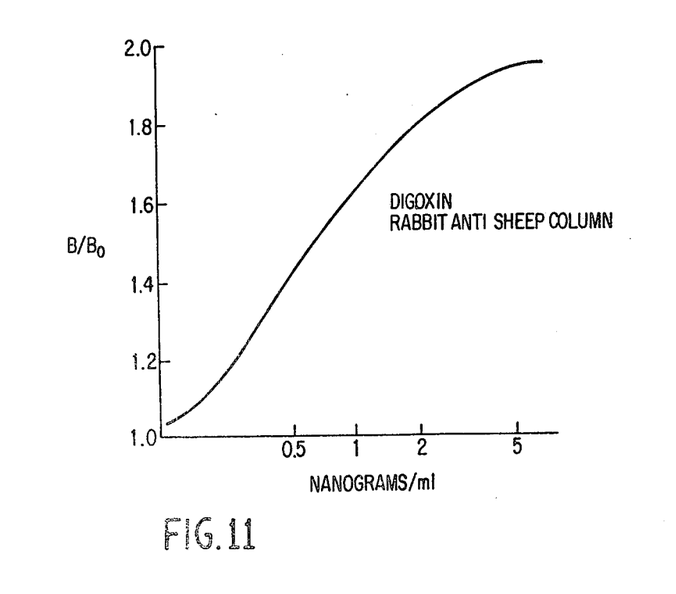
FIG. 11 is a standard curve for Digoxin using a rabbit, anti-sheep IgG column.

FIG. 11 demonstrates an immunoasay technique for digoxin. The initial incubation utilizes sheep anti-digoxin serum. Separation is achieved on a column containing immobilized Rabbit anti-sheep IgG.

Having now fully described the invention, it will be apparent to one or ordinary skill in the art that many changes and modifications can be made thereto without departing from the spirit or scope of the invention as set forth herein.

What is claimed as new and desired to be secured by Letters Patent of the Unites States is:

1. An automated immunoassay apparatus which comprises:
    means for time controlled incubation of a multiplicity of sample solutions, each of which comprises a mixture of (a) a sample, possibly containing an antigen or antibody intended to be assayed, (b) a solution of a known concentration of a tagged antigen or tagged antibody, and when assaying for antigen, optionally (c) a solution of a known titer of an antibody reactable with said antigen;
    activating detector means for determining the presence of the incubated sample and for activating a timing means upon detection of said sample at a detection station;
    means for introducing said incubated sample into said activating detector means;
    timing means, which is activatable by said activating detector means when said detector means detects the presence of the incubated sample at a detection station, for generating control signals at predetermined time sequences;
    means for separating said incubated sample into a first portion containing antigen or antibody which has not been complexed during the said incubation, and a second portion containing antigen or antibody which has been complexed during said incubation;
    means for introducing one of said portions from said separating means into a measuring detector means;
    measuring detector means for detecting the amount of tagged material in said portion while said portion is maintained in a virtually static condition;
    recording means coupled to said detector means for recording the amounts of tagged material in said measuring detector means;
    means for isolating said incubated sample from additional sample solutions introduced into said apparatus for assay, wherein said isolating means is activatable by a control signal emitted from said timing means, whereby said isolating means isolates the system at a first predetermined signal from said timing means, and whereby said isolating means reconnects the system to said incubation means at a second predetermined signal from said timing means, wherein the second predetermined time period is set so as to enable sufficient time to complete said measurement before the next incubated sample arrives in the said detector means for the next sequential measurement; and
    means for flushing said portion from said system after said measurement thereof so as to prepare said detector for the next sequential sample for said measurement.

2. The apparatus of claim 1 wherein said activating detector means is a conductivity detector for detecting changes in conductivity as a fluid is passed therethrough.

3. The apparatus of claim 1, wherein said activating detector means is a photodetection which is capable of detecting changes in solution turbidity.

4. The apparatus of claim 1, wherein said activating detector means is a colorimeter which is capable of determining the presence of dyes in said solution.

5. The apparatus of claim 1, wherein said activating detector means is a pH meter which is capable of detecting changes in solution pH.

6. The apparatus of claim 1, wherein said activating detector means is a refractometer which is capable of detecting changes in solids content of the solution as it is passed therethrough.

7. The apparatus of claim 1, wherein said measuring detector means is a colorimeter which is capable of detecting changes in solution color due to the presence of dye.

8. The apparatus of claim 1 wherein said measuring detector means is an enzyme substrate which is specific for a particular enzyme tagging material.

9. The apparatus of claim 1, wherein said measuring detector means is a radioactivity detector.

10. A method for continuous immunoassay, which comprises:
    incubating for a predetermined time period, a multiplicity of sample solutions, each of which comprises a mixture of (a) a sample possibly containing an antigen intended to be assayed; (b) a solution of a known concentration of a tagged antigen; and when assaying for antigen, optionally, (c) a solution containing a known titer of antibody reactable with said antigen, the concentration of said antibody being selected so as to form an incubated sample containing an antibody-antigen complex, and possibly containing unreacted antigen and tagged antigen, if said sample contains an antigen;

directing said incubated sample into an activating detector which is capable of determining the presence of said sample and activating, activating a timing means upon detection of said sample in said detector;

isolating said incubated sample from any additional samples being incubated on a predetermined signal from said timing means;

separating said incubated solution into a first portion containing an antigen or antibody which has not been complexed during the said incubation and a second portion containing antigen or antibody which has been complexed during said incubation;

directing one of said portions into a measuring detector, detecting the amount of tagged material in said portion while said portion is maintained in a virtually static condition, and recording said measurement;

evacuating said portion to waste;

directing a subsequent incubated sample into said activating detector on a second predetermined signal from said timing means so that the next subsequent incubated sample to be assayed arrives in the activating detector for the next measurement after the previous measurement is completed; and comparing the measurement with precalibrated values to determine the quantity of antigen being assayed.

11. The method of claim 10, wherein said samples contain antibodies intended to be assayed.

12. The method of claim 11, wherein said mixture contains a sample containing antibodies intended to be assayed and a solution of a known concentration of a tagged antigen.

13. The method of claim 10, wherein the presence of sample in said activating detector means is detected by change in pH or conductivity of said solution.

14. The method of claim 10, wherein the presence of sample in said activating detector means is detected by change in refractive index of said solution.

15. The method of claim 13, wherein the tagged antigen or antibody is tagged with a radioactive isotope and wherein measurement by said measuring means is effected by detection of quantity of radioactivity as a function of time.

16. The method of claim 10, wherein the tagged antigen or antibody is tagged with a dye and wherein measurement by said measuring means is effected by detection of color.

* * * * *

UNITED STATES PATENT OFFICE
CERTIFICATE OF CORRECTION

Patent No. 4,128,628                  Dated December 5, 1978

Inventor(s) Gary L. Brooker et al.

It is certified that error appears in the above-identified patent and that said Letters Patent are hereby corrected as shown below:

The term of this patent subsequent to

May 10, 1994, has been disclaimed.

Signed and Sealed this

Tenth Day of April 1979

[SEAL]

Attest:

RUTH C. MASON
Attesting Officer

DONALD W. BANNER
Commissioner of Patents and Trademarks